US006268513B1

(12) United States Patent
Guram et al.

(10) Patent No.: US 6,268,513 B1
(45) Date of Patent: *Jul. 31, 2001

(54) PHOSPHINE LIGANDS METAL COMPLEXES AND COMPOSITIONS THEREOF FOR CROSS-COUPLING REACTIONS

(75) Inventors: Anil Guram, San Jose; Xiaohong Bei, Sunnyvale, both of CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/378,107

(22) Filed: Aug. 20, 1999

Related U.S. Application Data

(63) Continuation-in-part of application No. 09/296,226, filed on Apr. 22, 1999.
(60) Provisional application No. 60/095,612, filed on Aug. 6, 1998.

(51) Int. Cl.[7] .................. C07D 321/00; C07C 255/00; C07C 2/00; C07F 9/02
(52) U.S. Cl. ..................... 549/200; 556/21; 558/411; 585/425; 562/493; 564/80; 564/161; 568/592; 549/491; 549/497
(58) Field of Search ............... 556/21; 558/411; 585/425; 562/493; 564/80, 161; 568/592; 549/200, 491, 497

(56) References Cited

U.S. PATENT DOCUMENTS

| | | | |
|---|---|---|---|
| 5,550,236 | 8/1996 | Schlosser et al. | 544/238 |
| 5,576,460 | 11/1996 | Buchwald et al. | 564/386 |
| 5,756,804 | 5/1998 | Haber et al. | 558/411 |
| 6,124,476 | * 9/2000 | Guram et al. | 549/200 |

FOREIGN PATENT DOCUMENTS

| | | |
|---|---|---|
| 2 239 970 | 6/1997 | (CA) . |
| WO 93/12260 | 6/1993 | (WO) . |
| WO 99/54337 | 10/1999 | (WO) . |
| WO 00/08032 | 2/2000 | (WO) . |

OTHER PUBLICATIONS

Old, D.W. et al, "A highly Active Catalyst for Palladium–Catalyzed Cross–Coupling Reactions . . . " J. AM Chem. Soc. 1998, 120 9722–9723.

Littke, A.F. et al "A Convenient and General Method for Pd–Catalyzed Suzuki Cross–Couplings of Aryl Chlorides and Arylboronic acids" Angew. Chem. Int. Ed. 1998, 37, No. 24 pp. 3387–3388.

Wolfe, J.P. et al, "A highly Active Catalyst for the Room–Temperature Amination and Suzuki Coupling of Aryl Chlorides", Angew. Chem. Int. Ed. 1999, 38, No. 16, pp. 2413–2416.

Wolfe, J.P., et al "Highly Active Palladium Catalysts for Suzuki Cross–Coupling Reactions" J. Am. Chem. Soc. 1999, 121, 9550–9561. pp. 9550–9561.

Drugs of the Future 1993, 18, 428–432.

Suzuki, "Cross–Coupling Reactions of Organoboron Compounds with Organic Halides" Diderich, F. Stang, P.J., Eds, Wiley–VCH:Weinheim, Germany, 1998, Chapter 2, pp. 49–97.

Shirakawa, E. "Iminophosphine–Palladium Catalyst for Cross–Coupling of Aryl Halides with Organostannanes" Tetrahedron Letters, vol. 38, No. 21, May 1997, pp. 3759–3762.

Horner, L. "Tertiare Phosphiine mit ortho–standig Chelatisierungsfahigen Funktionellen Gruppen . . . " Zeitschrifte fur Naturforschung, Tiel B, Anorganische Chemie, Organische Chemie, vol. 39b, No. 4 1984, pp. 504–511.

SchiemenzG.P., "Trilarylphosphine mith mehreren Carbonyl–Funktionen durch Grignard–Synthese" Justus Liebigs Annalen der Chemie, No. 9, 1973. pp. 1480–1493.

Vaughn, G.D., Synthesis and Reactivity of Stable Metallacyclic manganese and rhenium alpha–hydroxyalkyl complexes. J. Am. Chem. Soc. vol. 108, No. 7, 1986 pp. 1462–1473.

Trofimov, B. A. "Base–catalyzed addition of phosphine to aryl and hetarylethynes." Synthesis, No. 4, 1995 pp. 387–388.

Kamikawa, K. "Palladium–Catalyzed amination of aryl bromides utilizing arene–chromium complexes as ligands." J. Org. Chem. vol. 63, No. 23 Nov. 13, 1998 pp. 8407–8409.

Bei, X. et al, "General and Efficient Palladium–Catalyzed Aminations of Aryl Chlorides", Tetrahedron Letters, vol. 40. No. 7, Feb. 12, 1999. pp. 1237–1240.

Terfort, Andreas, et al. "Phosphane Ligands with two Binding Sites of Differeing Hardness for Enantioselective Grignard Cross–Coupling." J. Chem. Soc. Perkin. Trans. 1, pp. 1467–1479. (1996).

Meyers, Harold V., et al, "Multiple Simultaneous Synthesis of Phenolic Libraries." Molecular Diversity, vol. 1, pp. 13–20 (1995).

(List continued on next page.)

Primary Examiner—Porfirio Nazario-Gonzalez

(57) ABSTRACT

The present invention discloses new efficient processes for various bond forming reactions, including Suzuki reactions and aryl aminations. Organic compounds (e.g., ligands), their metal complexes and compositions using those compounds, provide useful catalysts. The invention also relates to performing Suzuki cross coupling reactions with unreactive aryl-chlorides.

18 Claims, No Drawings

OTHER PUBLICATIONS

Meyers, Harold V., et al. "Versitile Method of Parrallel Synthesis." Methods in Molecular and Cellular Biology, vol. 6, pp. 1–7, (1996).

Chemical Abstracts vol. 131, 1999 12–07 No. 2 (abstract of Organometallics, 1999 18 (10) 1840–1853).

Chemical Abstracts vol. 124 (1996) 09–04f No. 15 (Abstract of Bull. Korean Chem. Soc. 1995 16 (12) 1135–8).

Hellwinkel, Dieter, et al., "Polycyclic triaryldioxyphosphoranes of extreme stability," Chem. Bur., vol. 111, pp. 13–41, 1978.*

Hoots, John E., et al., "Substituted triaryl phosphines," Inorg. Synth., vol. 21, pp. 175–179, 1982.*

Frost, Christopher G., et al., "Enantiomerically pure acetals as ligands for asymmetric catalysis," Synlett, Issue 7, pp. 551–552, 1994.*

Newman, Louise M., et al., "Rhodium catalysed asymmetric hydrosilylation of ketones using phosphorus–containing oxazoline ligands," Tetrahedron: Asymmetry, vol. 7, No. 6, pp. 1597–1598, 1996.*

Grotjahn, D.B., et al., "Ruthenium alkoxycarbene complexes from an acetal function by C–O bond cleavage and alcohol elimination," Organometallics, vol. 15, pp. 2860–2862, 1996.*

Pian–pian, Xu, et al., "Synthesis, structure and hydrogenation property of trans–$PdCl_2\{Ph_2P[o-C_6H_4CH(OC_2H_2)]\}_2$" Chem. Res. Chin. Univ., vol. 13, No. 4, pp. 397–400, 1997.*

Pian–pian, Xu, et al., "Synthesis, characterization of new palladium complexes and their catalytic properties in hydrogenation reaction," Journal of Xiamen University, vol. 37, No. 1, pp. 52–57, 1998.*

* cited by examiner

PHOSPHINE LIGANDS METAL COMPLEXES AND COMPOSITIONS THEREOF FOR CROSS-COUPLING REACTIONS

BENEFIT CLAIM

This application is a continuation-in-part of U.S. patent application Ser. No. 09/296,226, filed Apr. 22, 1999, which claims the benefit of U.S. Provisional Application No. 60/095,612, filed Aug. 6, 1998. The disclosures of both applications are incorporated herein by reference.

RELATED APPLICATIONS

This application is related to U.S. patent application Ser. No. 09/062,128, filed Apr. 17, 1998 and of U.S. patent application Ser. No. 09/252,182, filed Feb. 18, 1999, the disclosures of both of which are incorporated herein by reference.

FIELD OF THE INVENTION

The present invention relates to a process for catalyzing cross coupling reactions (including Suzuki type cross coupling reactions) and aryl amination reactions using either a dicycloalkylphenyl phosphine or dialkylphenyl phosphine ligand, which may be in the form of a metal-ligand complex or metal precursor/ligand composition. In particular, this invention relates to improved processes that use phosphines, which when combined with suitable metals or metal precursor compounds provide useful catalysts for various bond-forming reactions.

BACKGROUND OF THE INVENTION

Ancillary (or spectator) ligand-metal coordination complexes (e.g., organometallic complexes) and compositions are useful as catalysts, additives, stoichiometric reagents, monomers, solid state precursors, therapeutic reagents and drugs. Ancillary ligand-metal coordination complexes of this type can be prepared by combining an ancillary ligand with a suitable metal compound or metal precursor in a suitable solvent under suitable reaction conditions. The ancillary ligand may contain functional groups that bind to the metal center(s), remain associated with the metal center(s), and therefore provide an opportunity to modify the steric, electronic and chemical properties of the active metal center(s) of the complex.

Certain known ancillary ligand-metal complexes and compositions are catalysts for reactions such as oxidation, reduction, hydrogenation, hydrosilylation, hydrocyanation, hydroformylation, polymerization, carbonylation, isomerization, metathesis, carbon-hydrogen activation, carbon-halogen activation, cross-coupling, hetero cross-coupling, Friedel-Crafts acylation and alkylation, hydration, amination, aryl amination, dimerization, trimerization, oligomerization, Diels-Alder reactions and other transformations.

One example of the use of these types of ancillary ligand-metal complexes and compositions is in the field of cross-coupling reactions. The palladium-catalyzed cross-coupling reactions of aryl-bromides, iodides, and triflates with alkyl or aryl-boron compounds provide a general and efficient route to a wide variety of substituted alkylphenyl or biphenyl compounds, and have now been extensively developed. See Suzuki, A. in *Metal-Catalyzed Cross-Coupling Reactions*; Diederich, F., Stang, P. J., Eds.; Wiley-VCH: Weinheim, Germany, 1998; Chapter 2, pp. 49–97, which is incorporated herein by reference. See also U.S. Pat. Nos. 5,550,236 and 5,756,804, both of which are incorporated herein by reference.

However, the related palladium-catalyzed reactions of the comparatively inexpensive and readily available aryl chlorides, which represent the most attractive candidates for industrial applications of these reactions, have been underdeveloped. See Old, D. W., Wolfe, J. P., Buchwald, S. L., *J Am. Chem. Soc.* 1998, 120, 9722–9723; and Littke, A. F., Fu, G. C., *Angew. Chem. Int. Ed. Eng.* 1998, 37, 3387–3388, which are both incorporated herein by reference. In particular, Buchwald et al. in the above referenced paper note that certain dicycloalkyl phosphine ligands are "not effective" for these palladium-catalyzed reactions. *J. Am. Chem. Soc.*, 1998 at 9723. In the supplemental material to that paper, Buchwald et al. disclose that in a palladium-dicyclohexylphenylphosphine catalyzed Suzuki cross-coupling reaction, the turn over number (TON) was about 9 after 2 days, giving a turn over frequency (TOF) of about 0.19.

This invention thus surprisingly demonstrates that improved catalytic activity can indeed be obtained with the exact ligands and catalyst systems that were previously characterized as "not effective." Compounds prepared according to the invention are suitable for use as precursors for pharmaceuticals, cosmetics, fungicides, herbicides, dyes, detergents, and polymers, including additives for these. Compounds prepared according to the invention are, in particular, valuable precursors for angiotensin II inhibitors. See *Drugs of the Future* 1993, 18, 428–432.

SUMMARY OF THE INVENTION

Thus, it is an object of this invention to provide a process for the cross coupling of reactants using ligand/metal compositions and/or metal-ligand complexes. These catalyst assisted chemical transformations obtain a turn over number (TON) of at least 50 and/or a turn over frequency (TOF) of at least 5, possibly with a selectivity in the range of from about 80% to about 100%. The ligand useful in this process can be characterized by the general formula:

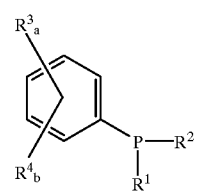

I wherein each $R^1$ and $R^2$ is independently selected from the group consisting of alkyl, substituted alkyl, cycloalkyl and substituted cycloalkyl. Each of $R^3$ is independently selected from the group consisting of alkyl, substituted alkyl, cycloalkyl, substituted cycloalkyl, heteroalkyl, heterocycloalkyl, substituted heterocycloalkyl, alyl, substituted aryl, heteroaryl, substituted heteroaryl, silyl, amino, nitro, ester, acid, alkoxy, aryloxy, hydroxy, transition metals, COOH, $SO_3G$ (G=Na, K, H, etc.) and combinations thereof; a is 0, 1 or 2 such that $R^3$, when present, occupies either the para position or the two meta positions. Each of $R^4$ is independently selected from the group consisting of alkyl, substituted alkyl, cycloalkyl, substituted cycloalkyl, heteroalkyl, heterocycloalkyl, substituted heterocycloalkyl, heteroaryl, substituted heteroaryl, silyl, amino, nitro, ester, acid, alkoxy, aryloxy, hydroxy, transition metals, COOH, $SO_3G$ (G=Na, K, H, etc.) and combinations thereof; b is 0, 1 or 2, such that when $R^4$ is present, it occupies either one or two ortho positions.

In a more particular embodiment, the preferred ligands of this invention may be characterized by the general formula:

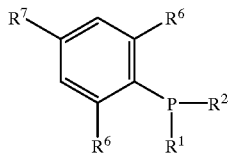

VI where $R^1$ and $R^2$ are as defined above and $R^6$ is selected from the same group as $R^4$ and $R^7$ is selected from the same group as $R^3$ or hydrogen.

The ligands are added to a metal precursor to provide a catalytic composition or metal-ligand complex. And, it is an object of this invention to provide improved processes using such compositions (i.e., comprising the ligand and a metal precursor) or metal complexes. The suitable metal or metal precursor compound can be of the form $ML_n$, where the composition has catalytic properties. Also, the ligands can be coordinated with a metal precursor to form metal-ligand complexes, which may be catalysts. Here, M is a transition metal selected from the group consisting of Groups 5, 6, 7, 8, 9 and 10 of the Periodic Table of Elements, preferably Pd, Ni, Ru, Rh, Pt, Co, Ir and Fe; L is independently each occurrence, a neutral and/or charged ligand; and n is a number 0, 1, 2, 3, 4, and 5, depending on M. M is most preferably Pd or Ni.

Another aspect of this invention is the chemical transformations that the new catalytic compositions or metal complexes enhance, and it is an object of this invention to provide catalysts and methods for such transformations. The compositions and metal complexes are useful as catalysts for various chemical transformations, particularly cross coupling reactions and aryl amination reactions. Specifically, the preparation of polycyclic aromatic compounds by a cross-coupling reaction of a first aromatic compound and second aromatic compound, more specifically with aromatic boron compounds and aromatic halogen compounds or perfluoroalkylsulfonates may be performed, and it is an object of this invention to provide catalysts and methods for such cross coupling reactions. The benefit of using these catalysts in such reactions is generally higher conversions (e.g., turnovers) when using less costly starting materials.

Further aspects of this invention will be evident to those of skill in the art upon review of this specification.

DETAILED DESCRIPTION OF THE INVENTION

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$ or $R^4$ can be identical or different (e.g. $R^1$, $R^2$ and $R^3$ may all be substituted alkyls or $R^1$ and $R^4$ may be a substituted alkyl and $R^3$ may be an aryl, etc.). A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom to any carbon of the alkyl is replaced by another group such as a halogen, aryl, substituted aryl, cycloalkyl, substituted cycloalkyl, and combinations thereof. Suitable substituted alkyls include, for example, benzyl, trifluoromethyl and the like.

The term "heteroalkyl" refers to an alkyl as described above in which one or more hydrogen atoms to any carbon of the alkyl is replaced by a heteroatom selected from the group consisting of N, O, P, B, S, Si, Se and Ge. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethylaminocyclohexyl, 4,5-dibromocyclohept-4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorous, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl, and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholine, and the like.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, biphenyl, diphenylether, diphenylamine and benzophenone among others. In particular embodiments, aryls have between 6 and 200 carbon atoms, between 6 and 50 carbon atoms or between 6 and 20 carbon atoms.

"Substituted aryl" refers to aryl as just described in which one or more hydrogen atom to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, phosphino, alkoxy, aryloxy, amino, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone.

The term "heteroaryl" as used herein refers to aromatic rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Substituted heteroaryl" refers to heteroaryl as just described including in which one or more hydrogen atoms to any atom of the heteroaryl moiety is replaced by another group such as a halogen, alkyl, substituted alkyl, aryl, substituted aryl, heteroaryl, substituted heteroaryl, alkoxy, aryloxy, hydroxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the —$OZ^1$ radical, where $Z^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the —$SiZ^1Z^2Z^3$ radical, where each of $Z^1$, $Z^2$, and $Z^3$ is independently selected from the group consisting of alkyl, substituted alkyl, cycloalkyl, substituted cycloalkyl, heterocylcoalkyl, substituted heterocycloalkyl, aryl, substituted aryl, heteroaryl, substituted heteroaryl, alkoxy, aryloxy, amino, silyl and combinations thereof.

As used herein the term "boryl" refers to the —$BZ^1Z^2$ group, where each of $Z^1$ and $Z^2$ is independently selected from the group consisting of alkyl, substituted alkyl, cycloalkyl, substituted cycloalkyl, heterocylcoalkyl, substituted heterocycloalkyl, aryl, substituted aryl, heteroaryl, substituted heteroaryl, alkoxy, aryloxy, amino, silyl and combinations thereof.

The term "amino" is used herein to refer to the group —$NZ^1Z^2$, where each of $Z^1$ and $Z^2$ is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof. Additionally, the amino group may be present as $N^+Z^1Z^2Z^3$, with the previous definitions applying and $Z^3$ being either H or alkyl.

The ligands useful in this invention can be characterized by the general formula:

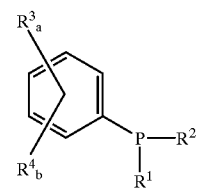

I wherein each $R^1$ and $R^2$ is independently selected from the group consisting of alkyl, substituted alkyl, cycloalkyl and substituted cycloalkyl; and Each of $R^3$ is independently selected from the group consisting of alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, silyl, amino, nitro, ester, acid, alkoxy, aryloxy, hydroxy, transition metals, COOH, $SO_3G$ (G=Na, K, H, etc.) and combinations thereof; a is 0, 1 or 2 such that $R^3$, when present, occupies either the para position or the two meta positions. Each of $R^4$ is independently selected from the group consisting of alkyl, substituted alkyl, cycloalkyl, substituted cycloalkyl, heteroalkyl, substituted heteroalkyl, heterocycloalkyl, substituted heterocycloalkyl, heteroaryl, substituted heteroaryl, silyl, amino, nitro, ester, acid, alkoxy, aryloxy, hydroxy, transition metals, COOH, $SO_3G$ (G=Na, K, H, etc.) and combinations thereof; b is 0, 1 or 2, such that when $R^4$ is present, it occupies either one or two ortho positions. When $R^3$ or $R^4$ is absent, a hydrogen atom is present in its place.

In more specific embodiments, each $R^1$ and $R^2$ is independently selected from a group consisting of alkyl, substituted, cycloalkyl and substituted cycloalkyl, with specific examples including cyclopentyl, cylcohexyl, cyclooctyl, and the like. Cyclohexyl is preferred.

More specifically, each $R^3$ may be chosen from the group consisting of alkyl, substituted alkyl, cycloalkyl, substituted cycloalkyl, heterocycloalkyl, substituted heterocycloalkyl, aryl, substituted aryl, heteroaryl, substituted heteroaryl, silyl, amino, alkoxy, aryloxy, phosphino, boryl, transition metals, metallocenes, halogens and combinations thereof. Specific examples of include methyl, ethyl, propyl, t-butyl, phenyl, methoxy, alkoxy, thioalkyl, cyano, acetyl, benzoyl, nitro, dimethylamino, diethylamino, methylphenylamino, benzylmethylamino, trimethylsilyl, dimethylboryl, diphenylboryl, methylphenylboryl, dimethoxyboryl, chromium tricarbonyl, ruthenium tricarbonyl, and cyclopentadienyl iron. $R^3$ can also be a water-solubilizing group, such as $SO_3G$, where G is Na, K, H and the like. $R^3$ may also be a transition metal that is eta bonded to the benzene ring in the backbone of the ligand.

More specifically, each $R^4$ may be chosen from the group consisting of alkyl, substituted alkyl, cycloalkyl, substituted cycloalkyl, heterocycloalkyl, substituted heterocycloalkyl, heteroaryl, substituted heteroaryl, silyl, amino, alkoxy, aryloxy, phosphino, boryl, transition metals, metallocenes, halogens and combinations thereof. Specific examples of include methyl, ethyl, propyl, t-butyl, methoxy, alkoxy, thioalkyl, cyano, acetyl, benzoyl, nitro, dimethylamino, diethylamino, methylphenylamino, benzylmethylamino, trimethylsilyl, chromium tricarbonyl, ruthenium tricarbonyl, and cyclopentadienyl iron. $R^4$ can also be a water-solubilizing group, such as $SO_3G$, where G is Na, K, H and the like. $R^4$ may also be a transition metal that is eta bonded to the benzene ring in the backbone of the ligand.

In a more particular embodiment, preferred ligands of this invention may be characterized by the general formula:

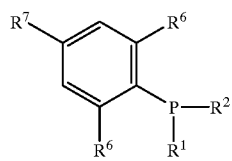

VI where $R^1$ and $R^2$ are as defined above and $R^6$ is selected from the same group as $R^4$ and $R^7$ is either hydrogen or selected from the same group as $R^3$. Specific preferred embodiments of $R^6$ and $R^7$ are alkyl and substituted alkyl and cycloalkyl and substituted cycloalkyl, specifically isopropyl, cyclopentyl, cyclohexyl, cyclooctyl, cycloheptyl, isobutyl, and tert-butyl. $R^7$ can also be hydrogen. Without wishing to be bound by any particular theory or mechanism, it is believed that the $R^7$ group has substantially less impact on the catalytic performance of the ligand when used as part of the catalyst in cross coupling or aryl amination reactions. Thus, changes in the $R^7$ group may be useful for specific reactions or reaction conditions, but may not have a substantial impact.

In an alternative embodiment, the phosphine ligands useful in this invention have a cyclopentadienyl ring, and may be characterized by the formula:

II where $R^1$ and $R^2$ are defined as above and each $R^5$ is independently selected from the group consisting of alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, silyl, amino, nitro, ester, acid, alkoxy, aryloxy, hydroxy, metallocene, transition metals, COOH, $SO_3G$ (G=Na, K, H, etc.) and combinations thereof; c is 0, 1, 2, 3 or 4 and $R^5$ can occupy any available site on the cyclopentadienyl ring, including an eta-bond (such as an $\eta^5$ bond). More specific embodiments of $R^5$ are those where a mono-cyclopentadienyl or bis-cyclopentadienyl metallocene is formed as part of the ligand. Thus, $R^5$ may be a moiety having a metal atom selected from the group consisting of metals from the Periodic Table of Elements, such as Fe, Rh, Mo, Ru, Cr, Zr, Ti, Hf, Co. Specific examples of $R^5$ include FeCp, CrCp and $ZrCpR_2$, where Cp is a substituted or unsubstituted cyclopentadienyl and R is selected from the same group as $R^5$. In this specific embodiment, it is intended that the bond between the Cp ring in the ligand and $R^5$ is an $\eta^5$ bond.

Particularly preferred ligands are:

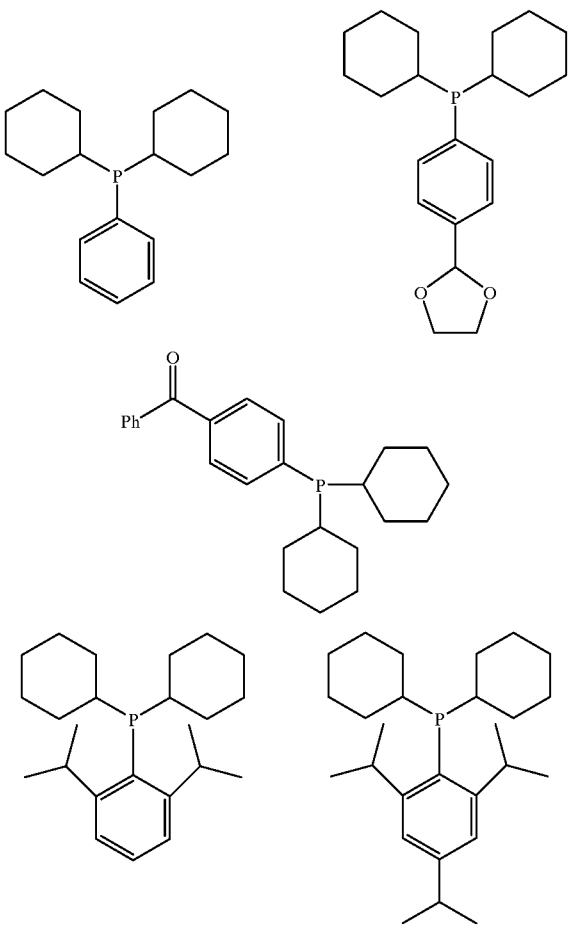

The ligands useful in this invention may be on a support or not. For example, the support could be any one of the R groups. In that embodiment, the support may be a polymer or functionalized polymer, such as polystyrene. In the case of heterogeneous reactions, the ligands may be supported, with or without the metal coordinated (discussed below), on an organic or inorganic support. Suitable supports include silicas, aluminas, zeolites, polyethyleneglycols, polystyrenes, polyesters, polyamides, peptides and the like.

The ligand is combined with a metal atom, ion, compound or other metal precursor compound. In many applications, the ligands of this invention will be combined with such a metal compound or precursor and the product of such combination is not determined, if a product forms. For example, the ligand may be added to a reaction vessel at the same time as the metal or metal precursor compound along with the reactants. The metal precursor compounds may be characterized by the general formula $M(L)_n$ (also referred to as $ML_n$ or $M-L_n$) where M is a metal selected from the group consisting of Groups 5, 6, 7, 8, 9 and 10 of the Periodic Table of Elements. In more specific embodiments, M is selected from the group consisting of Ni, Pd, Fe, Pt, Ru, Rh, Co and Ir. L is a ligand chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof. When L is a charged ligand, L is selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. When L is a neutral ligand, L is selected from the group consisting of carbon monoxide, isocyanide, nitrous oxide, $PA_3$, $NA_3$, $OA_2$, $SA_2$, $SeA_2$, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino. Specific examples of suitable metal precursor compounds include $Pd(dba)_2$ (dba=dibenzylydieneacteone), $Pd_2(dba)_3$, $Pd(OAc)_2$ (Ac=acetate), $PdCl_2$, $Pd(TFA)_2$, (TFA= trifluoroacetate), $(CH_3CN)_2PdCl_2$, and the like. In this context, the ligand to metal precursor compound ratio is in the range of about 0.01:1 to about 100:1, more preferably in the range of about 0.5:1 to about 20:1. The metal atom, ion or metal precursor may be supported or not. Supports may be organic or inorganic. Similar to the ligands, the support may be a L. In other embodiments, the support will not form part of the metal precursor and suitable supports include silicas, aluminas, zeolites, polyethyleneglycols, polystyrenes, polyesters, polyamides, peptides and the like. Specific examples of Pd supported metals include Pd/C, $Pd/SiO_2$, $Pd/CaCO_3$, $Pd/BaCO_3$, Pd/aluminate, Pd/aluminum oxide, Pd/polystyrene, although any of the metals listed above could replace Pd in this list, e.g., Ni/C, etc.

In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be a catalyst. By way of example only, the metal complexes may be characterized by the formula:

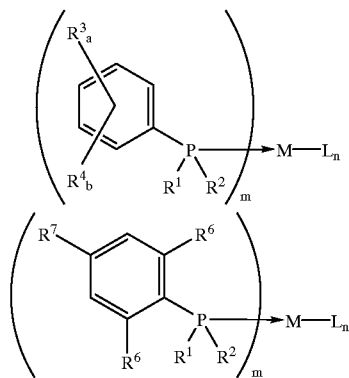

III where $R^1$, $R^2$, $R^3$, $R^4$, $R^6$, $R^7$, M, L, a, b and n have the definitions given above and additionally m is a number that is 1, 2 or 3.

Generally, the ligands useful in this invention may be purchased or prepared methods known to those of skill in the art. Specific synthesis methods are shown in Examples 1 and 2. See, for example, Goetz, H., et al., *Liebigs Ann. Chem.* (1977), No. 4, pp. 556–564. For synthesis of some preferred embodiments of the ligands of this invention, a metal catalyzed phosphorus-carbon bond may be formed as shown in Scheme 1, below:

Scheme 1

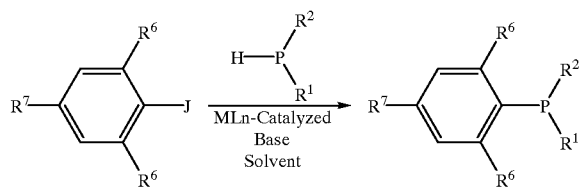

where the symbols in Scheme 1 have the same meanings as discussed herein and J is selected from the group consisting of Br, I, Cl, tosylates, triflates and nonaflates. In Scheme 1, the coupling reaction changes depending on J. When J is H or Br, the reaction comprises the addition of a butyl lithium reagent (e.g., n-BuLi or s-BuLi or t-BuLi) followed by addition of $ClPR^1R^2$ or $BrPR^1R^2$. When J is F, the reaction comprises addition of a reagent that is characterized by $M''PR^1R^2$ where M'' is either Li, Mg, Zn or K. Finally, when J is Br, I, Cl, a tosylate, a triflate or a nonaflate, the reaction in Scheme 1 comprises a metal catalyzed cross-coupling reaction with $M'''PR^1R^2$ where M''' is H, $SiR_3$ (with R=alkyl, aryl or cycloalkyl) or M''. The catalyst for this reaction is a suitable metal, such as Pd or Ni, optionally with a ligand, such as is generally known to those skilled in the art.

The catalyst compositions and metal complexes of this invention are useful for many metal-catalyzed reactions, particularly for Suzuki cross-coupling reactions with aryl chlorides. In general, this invention may be effectively employed for metal-catalyzed coupling of organometallic reagents with organic electrophiles; metal-catalyzed coupling of organometallic reagents with organic halides; metal-catalyzed coupling of organometallic reagents with aryl halides and vinyl halides; and metal-catalyzed coupling of organometallic reagents with aryl chlorides. In particular, the following reactions can be effectively performed with this invention: aryl-aryl or biaryl coupling reactions, including coupling of aryl boron reagents (aryl boronic acid and esters) with aryl halides including aryl chlorides, aryl triflates, aryl tosylates, aryl mesylates (Suzuki coupling); coupling of aryl zinc reagents with the compounds as above; coupling of aryl magnesium reagents with the compounds as above; coupling of aryl tin reagents with the compounds as above; and coupling of aryl metal reagents with the compounds as above. Those of skill in the art will recognize that this list can be repeated by simply substituting heteroaryl for aryl without departing from the scope of this invention. Additional reactions that can be effectively performed with this invention include vinyl-aryl coupling reactions such as the coupling of vinyl metal reagents with the compounds as above, coupling of vinyl aluminate reagents with the compounds as above, coupling of vinyl cuprate reagents with the compounds as above, coupling of vinyl zirconium reagents with the compounds as above; and the coupling of vinyl boron reagents with the compounds as above. Still further, reactions that can be effectively performed with this invention include reactions which involve oxidative addition, transmetallation and reductive elimination sequence or oxidative addition, insertion or beta-hydride elimnation sequence in the catalytic cycle, including Heck reactions that involve metal-catalyzed olefination of aryl halides including chloride, aryl mesylates, tosylates, aryl triflates. Other reaction examples, include Sonogashira, cyanation, aryl amination, Stille coupling, Castro-Stephens, and hydrogenations.

To carry out the process of this invention for one type of reaction, a first aromatic compound, a second aromatic compound, a base, a catalytic amount of metal precursor and a catalytic amount of the ligand are added to an inert solvent or inert solvent mixture. In a batch methodology, this mixture is stirred at a temperature of from 0° C. to 200° C., preferably at from 30° C. to 170° C., particularly preferably at from 50° C. to 150° C., most particularly preferably at from 60° C. to 120° C., for a period of from 5 minutes to 100 hours, preferably from 15 minutes to 70 hours, particularly preferably from ½ hour to 50 hours, most particularly preferably from 1 hour to 30 hours. After the reaction is complete, the catalyst may be obtained as solid and separated off by filtration. The crude product is freed of the solvent or the solvents and is subsequently purified by methods known to those skilled in the art and matched to the respective product, e.g. by recrystallization, distillation, sublimation, zone melting, melt crystallization or chromatography.

Solvents suitable for the process of the invention are, for example, ethers (e.g., diethyl ether, dimethoxymethane, diethylene glycol, dimethyl ether, tetrahydrofuran, dioxane, diisopropyl ether, tert-butyl methyl ether), hydrocarbons (e.g., hexane, iso-hexane, heptane, cyclohexane, benzene, toluene, xylene), alcohols (e.g., methanol, ethanol, 1-propanol, 2-propanol, ethylene glycol, 1-butanol, 2-butanol, tert-butanol), ketones (e.g., acetone, ethyl methyl ketone, iso-butyl methyl ketone), amides (e.g., dimethylformamide, dimethylacetamide, N-methylpyrrolidone), nitriles (e.g., acetonitrile, propionitrile, butyronitrile), water and mixtures thereof. Particularly preferred solvents are ethers (e.g., dimethoxyethane, tetrahydrofuran), hydrocarbons (e.g., cyclohexane, benzene, toluene, xylene), alcohols (e.g., ethanol, 1-propanol, 2-propanol), water and combinations thereof. Most particularly preferred are dimethoxyethane, benzene, toluene, xylene, dioxane, ethanol, water and combinations thereof.

Bases which are useful in the process of the invention are alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides, alkali metal and alkaline earth metal phosphates, primary, secondary and tertiary amines, alkali metal and alkaline earth fluorides, and ammonium fluorides. Particularly preferred are alkali metal and alkaline earth metal phosphates, alkali metal and alkaline earth metal carbonates, alkali metal hydrogen carbonates, alkali metal and alkaline earth fluorides, and ammonium fluorides. Most particularly preferred are alkali metal phosphates and alkali metal and alkaline earth metal fluorides (such as potassium phosphate and cesium fluoride). The base is preferably used in the process of the invention in an amount of from about 1 to about 1000 mol %, particularly preferably from about 50 to about 500 mol %, very particularly preferably from about 100 to about 400 mol %, in particular from about 150 to about 300 mol %, based on the aromatic boronic acid.

The metal precursor used is as described above and may be added to the process along with the reactants. The metal portion of the catalyst (metal precursor or metal complex) is used in the process of this invention in a proportion of from about 0.0001 to about 10 mol %, preferably from about 0.1 to about 5 mol %, particularly preferably from about 0.5 to about 3 mol %, most particularly preferably from about 1.0 to about 1.5 mol %, based on the second aromatic compound. The ancillary ligand is used in the process in a proportion of from about 0.0001 to about 20 mol %, preferably from about 0.2 to about 15 mol %, particularly preferably from about 0.5 to about 10 mol %, most particularly preferably from about 1 to about 6 mol %, based on the second aromatic compound. These amounts may be combined to give metal precursor to ligand ratios useful in the process. It is also possible, if desired, to use mixtures of two or more different ligands.

The first aromatic compounds for the process may be characterized by either of the general formulas:

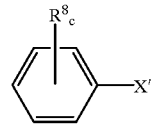

IV

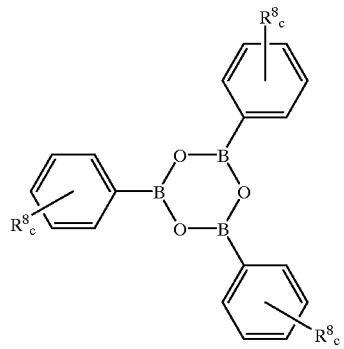

V where $R^8$ is selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; c is 0, 1, 2, 3, 4 or 5 and optionally two or more $R^8$ groups are joined together in a ring structure; X' is selected from the group consisting of $BR^{10}{}_2$, $B(OR^{10})_2$, $MgQ^1$, $ZnQ^1$, $CuQ^1$, $SiR^{10}{}_3$, $SnR^{10}{}_3$ or Li, wherein each $R^{10}$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, hydroxy, silyl, boryl, phosphino, amino, thio, seleno, and combinations thereof; and $Q^1$ is selected from the group consisting of Cl, Br, I or F. See also U.S. Pat. No. 5,756,804, incorporated herein by reference for other, similar formulas.

The second aromatic compounds for the process of the invention those of the formula:

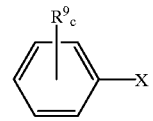

where X is Br, Cl, F, I, tosylates, triflates, or $N_2^+$ and $R^9$ is selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; and c is 0, 1, 2, 3, 4 or 5. Optionally two or more $R^9$ groups are joined together in a ring structure. Preferable, $R^9$ is selected from the group consisting of methyl, ethyl, methoxy, —CN and —CF$_3$. See also U.S. Pat. No. 5,756, 804, incorporated herein by reference for other, similar formulas.

Products of the process of the invention are polycyclic aromatic compounds having an aryl-aryl bond, having the general structure:

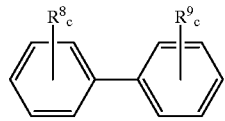

The products are also suitable as precursors for pharmaceuticals, cosmetics, fungicides, herbicides, insecticides, dyes, detergents and polymers, including additives for the same. Aryl amination reactions have similar usefulness, e.g., U.S. Pat. No. 5,576,460, incorporated herein by reference.

The processes of this invention are particularly effective in performing the above-disclosed chemical transformations. Turn over numbers (TON), which are calculated as the moles of desired product divided by the moles of metal precursor, are typically at least about 50, preferably at least 100, and more preferably at least 200, but can range to at least 500 or even at least 1000. Turn over frequency (TOF), which is calculated as the TON divided by the reaction time in hours, are typically at least about 5, preferably at least 10, more preferably at least 20, and more preferably at least 50, but can range to at least 100 or even at least 200. Selectivity for the reaction to produce the desired product (as compared to undesired side products) are also in the range of from at least 80% to approaching 100%, with selectivity in the range of from about 90% to about 99% being common. Selectivity is calculated as 100 times units of desired product divided by the sum of the units of desired product plus the units of undesired product. As the TON's, TOF's and selectivity numbers imply, the yield from the processes of this invention are typically greater than 90%.

EXAMPLES

General

All reactions were performed under argon atmosphere in oven-dried glass Schlenk tubes using standard Schlenk techniques. All aryl halides, aryl boronic acids, bases, bis(dibenzylideneacetone)palladium, and solvents were purchased from commercial sources and used as such. All solvents were of the anhydrous, sure-seal grade. Phenyldicyclohexylphosphine (PhPCy$_2$; ligand 1) was also purchased from a commercial source. The detailed procedure described for the synthesis and isolation of 2-Acetyl-4'-methyl-1,1'-biphenyl (example 3) was generally followed for all Pd/Ligand-catalyzed Suzuki reactions of arylboronic acids with aryl halides (examples 4–10). Column chromatography was performed using commercially available Silica Gel 60 (particle size: 0.063–0.100 mm), hexanes and ethyl acetate. GC-MS analyses were conducted on a Hewlett-Packard 6890 instrument. $^1$H, $^{13}$C, $^{31}$P NMR spectra were obtained using a Bruker 300 MHz FT-NMR spectrometer. Chemical shifts in $^1$H, and $^{13}$C NMR spectra were calibrated with reference to the chemical shift of residual protiated solvent. Chemical shifts in $^{31}$P NMR spectra were calibrated with reference to 85% H$_3$PO$_4$; a negative value of chemical shift denotes resonance upfield from H$_3$PO$_4$. Coupling constants are reported in hertz. TON and TOF were calculated as discussed above.

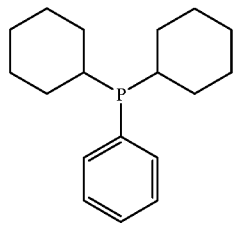

Ligand 1

Example 1

This is an example of synthesis of ligand 2
2-(4'-Dicyclohexylphosphinophenyl)-1,3-dioxolane (Ligand 2)

Part I

A solution of 4-bromobenzaldehyde (5 g, 0.027 mol), ethylene glycol (7.0 g, 0.11 mmol), and p-toluenesulfonic acid (0.1 g, 0.5 mmol) in benzene was heated at reflux for 24 h using a Dean-Stark setup to remove water. The reaction was taken up in diethyl ether (100 mL) and washed with water (5×30 mL) and brine (30 mL). The organic phase was dried over magnesium sulfate and concentrated under vacuum to afford 2-(4'-bromophenyl)-1,3-dioxolane (5.95 g).

Part II 2-(4'-bromophenyl)-1,3-dioxolane (1.0 g, 4.4 mmol) was dissolved in anhydrous diethyl ether (30 mL) and the solution was cooled to –78° C. t-Butyllithium (5.14 mL, 1.7 M solution in pentane, 8.8 mmol) was added dropwise with stirring. The reaction was stirred for 2 h at –78° C. Chlorodicyclohexylphosphine (1.13 g, 4.8 mmol) was added dropwise via a syringe at –78° C. with stirring. The reaction mixture was allowed to warm up to room temperature and stirred for an additional 18 h. To the reaction mixture was added argon purged water (25 mL) slowly. The organic phase was separated under argon and the aqueous phase was washed with diethyl ether (20 mL). The combined organic phase was concentrated under vacuum to afford a colorless oil, which was crystallized from methanol to afford ligand 2 as a white crystalline solid having the structure shown below (yield: 1.4 g, 92%). $^{31}$P{$^1$H} NMR (CDCl$_3$): δ2.4.

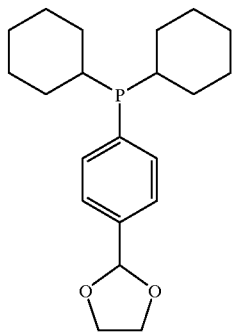

Ligand 2

Example 2

This is an example of synthesis of ligand 3
4-Dicyclohexylphosphino-benzophenone (Ligand 3)

o-Xylene (4 mL) and dicyclohexylchlorophosphine (0.20 mL, 1.0 mmol) were added to the mixture of 4-bromobenzophenone (261 mg, 1.0 mmol), NaO$^t$Bu (96 mg, 1.0 mmol), Pd(dba)$_2$ (11 mg, 19 μmol) under Ar. The mixture was heated from 85 to 110° C. in 15 min and remained at 110° C. for an additional 1.5 h. The reaction mixture was filtered through a 2 g silica gel column (Aldrich) and hexanes/ethyl acetate (1:1) was used as elute. The filtrate was concentrated under vacuum, yielding a red oil. The oil was re-crystallized from MeOH (1.0 mL) at −30° C. overnight, yielding ligand 3 as a yellow solid (233 mg, 62%) after filtration and drying under vacuum. $^{31}$P NMR (CDCl$_3$): δ6 3.8.

Ligand 3

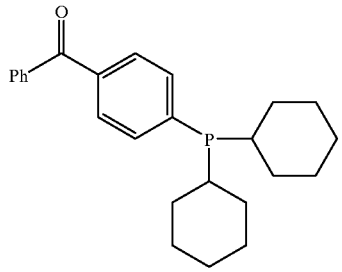

Example 3

This is an example of Pd/ligand 1-catalyzed Suzuki reaction for biaryl synthesis
2-Acetyl-4'-methyl-1,1'-biphenyl A solid mixture of 4-methylphenylboronic acid (204 mg, 1.5 mmol), CsF (456 mg, 3.0 mmol), Pd(dba)$_2$ (3 mg, 5 μmol), and ligand 1 (5 mg, 15 μmol) was thoroughly evacuated and purged with argon. 2'-Chloroacetophenone (0.13 mL, 1.0 mmol) and toluene (4 mL) were added and the reaction was heated at 110° C. for 1 h. GC-MS analysis indicated the reaction to be complete, i.e. starting aryl chloride reagent was completely consumed (quantitative GC yield). The reaction was taken up in ether (100 mL) and washed with H$_2$O (30 mL) and brine (30 mL), The organic phase was dried over MgSO$_4$, filtered and concentrated under vacuum. The crude product was purified by column chromatography on silica gel using hexanes:ethyl acetate (8:1) as eluant to afford the title compound as a yellow oil (198 mg, 92% isolated yield) after drying under vacuum. TON≈100 and TOF≈100. $^1$H NMR (CDCl$_3$): δ7.52 (d, J=8.4, 1H, ArH), 7.47 (d, J=7.2, 1H, ArH), 7.38 (t, J=7.2, 2H, ArH), 7.22 (s, 4H, ArH), 2.39 (s, 3H, C(O)CH$_3$), 2.00 (s, 3H, ArCH$_3$). $^{13}$C{$^1$H} NMR (CDCl$_3$): δ205.1, 140.9, 140.5, 137.8, 137.7, 130.6, 130.2, 129.4, 128.7, 127.8, 127.2, 30.4, 21.2.

Example 4

This is an example of Pd/ligand 1-catalyzed Suzuki reaction for biaryl synthesis.
3,5-Dimethylbiphenyl The title compound was obtained as a colorless oil (184 mg, 99% isolated yield) from the reaction of phenylboronic acid (190 mg, 1.56 mmol), CsF (473 mg, 3.12 mmol), Pd(dba)$_2$ (6 mg, 10 μmol), ligand 1 (11 mg, 31 μmol), and 5-chloro-m-xylene (0.14 mL, 1.0 mmol) in toluene at 110° C. for 5 h. TON≈100 and TOF≈20. $^1$H NMR (CDCl$_3$): δ7.64 (d,J=8.1, 2H, ArH), 7.47 (t,J=7.7, 2H, ArH), 7.35 (t, J=7.5, 1H, ArH), 7.27 (s, 2H, ArH), 7.05 (s, 1H, ArH), 2.44 (s, 6H, ArCH$_3$'s). $^{13}$C{$^1$H} NMR (CDCl$_3$): δ141.5, 141.3, 138.2, 128.9, 128.6, 127.2, 127.0, 125.1, 21.4.

Example 5

This is an example of Pd/ligand 1-catalyzed Suzuki reaction for biaryl synthesis
2,2'-Dimethyl-1,1'-biphenyl The title compound was obtained as a yellowish oil (180 mg, 97% isolated yield) from the reaction of 2-methylphenylboronic acid (203 mg, 1.54 mmol), CsF (469 mg, 3.09 mmol), Pd(dba)$_2$ (11.8 mg, 21 μmol), ligand 1 (22 mg, 61 μmol), and 2-chlorotoluene (0.12 mL, 1.03 mmol) in toluene (4 mL) at 110° C. for 5 h. TON=49 and TOF=9.8. $^1$H NMR (CDCl$_3$): δ7.32–7.18 (m, 6H, ArH), 7.13 (d, J=6.2, 2H, ArH), 2.08 (s, 6H, CH$_3$'s). $^{13}$C{$^1$H} NMR (CDCl$_3$): δ141.6, 135.8, 129.8, 129.3, 127.1, 125.5, 19.8.

Example 6

This is an example of Pd/ligand 1-catalyzed Suzuki reaction for biaryl synthesis. A reaction mixture of CsF (0.764 g, 5.06 mmol), 2-chlorobenzonitrile (0.307 g, 2.24 mmol), and p-tolueneboronic acid (0.329 g, 2.42 mmol), Pd(dba)$_2$ (1 mg, 1.7 μmol), and ligand 1 (5 mg, 18 μmol) in toluene (4 mL) was heated at reflux and monitored by GC-MS. After 3.5 h, GC-MS analysis showed a >98% GC yield of the desired product 2-cyano-4'-methylbiphenyl. TON=1318 and TOF =377.

Example 7

This is an example of Pd/ligand 1-catalyzed Suzuki reaction for biaryl synthesis. A reaction mixture of CsF (0.764 g, 5.06 mmol), 2-chlorobenzonitrile (0.230 g, 1.68 mmol), and p-tolueneboronic acid (0.329 g, 2.42 mmol), Pd(dba)$_2$ (2 mg, 3.4 μmol), and ligand 1 (5 mg, 18 μmol) in 1,4-dioxane (4 mL) was heated at reflux and monitored by GC-MS. After 8 h, GC-MS analysis showed a >98% GC yield of the desired product 2-cyano-4'-methylbiphenyl. TON=494 and TOF=62.

Example 8

This is an example of Pd/ligand 3-catalyzed Suzuki reaction for biaryl synthesis. A reaction mixture of CsF (0.750 g, 4.97 mmol), 2-chlorobenzonitrile (0.230 g, 1.68 mmol), and p-tolueneboronic acid (0.329 g, 2.42 mmol), Pd(dba)$_2$ (1 mg, 1.7 μmol), and ligand 3 (5 mg, 7.6 μmol) in 1,4-dioxane (4 mL) was heated at reflux and monitored by GC-MS. After 19 h, GC-MS analysis showed a >98% GC yield of the desired product 2'-cyano-4-methylbiphenyl. TON =988 and TOF =52.

Example 9

This is an example of Pd/ligand 2-catalyzed Suzuki reaction for biaryl synthesis.
3,5-Dimethylbiphenyl A reaction mixture of phenylboronic acid (190 mg, 1.56 mmol), CsF (474 mg, 3.12 mmol), Pd(dba)$_2$ (6 mg, 10 μmol), ligand 2 (10 mg, 29 μmol), and 5-chloro-m-xylene (0.14 mL, 1.0 mmol) in toluene (4 mL) was heated at reflux and monitored by GC-MS. After 5 h, GC-MS analysis showed a >98% GC yield of the desired product 3,5-dimethylbiphenyl. TON=100 and TOF=20.

Comparative Example 10

This is an example of Pd(dba)$_2$-catalyzed Suzuki reaction for biaryl synthesis in the absence of a ligand. A reaction mixture of phenylboronic acid (190 mg, 1.56 mmol), CsF (474 mg, 3.12 mmol), Pd(dba)$_2$ (6 mg, 10 μmol), and 5-chloro-m-xylene (0.14 mL, 1.0 mmol) in toluene (4 mL) was heated at reflux and monitored by GC-MS. After 5 h, GC-MS analysis showed no product formation.

Example 11

This is an example for the synthesis of 2,4,6-(Triisopropylphenyl)dicyclohexylphosphine (Ligand 4), shown below. A solid mixture of NaO$^t$Bu (600 mg, 6.24 mmol) and Pd(dba)$_2$ (76 mg, 0.13 mmol) was evacuated thoroughly and purged with argon. 2,4,6-Triisopropylbromobenzene (1.13 g, 4.0 mmol), HPCy$_2$ (0.88 mL, 4.35 mmol) and o-xylene (16 mL) were added. The mixture was heated from 105–140° C. in 15 min and kept at 140° C. for 35 h. The reaction mixture was filtered through a SiO$_2$ column and the column was washed with toluene (30 mL). The filtrate was concentrated under vacuum and the oily residue was triturated with deoxygenated MeOH, affording ligand 4, after filtration and drying under vacuum, as a white solid (0.55 g, 34%, yield not optimized). $^1$H NMR (CDCl$_3$): δ6.96 (d, J=4.2, 1 H, ArH), 6.90 (s, 1H, ArH), 4.43 (sept, J=6.7, 1H, CH), 3.33 (sept, J=6.6, 1H, CH), 2.83 (sept, J=6.9, 1H), 2.17 (m, 2H), 1.98 (br, 2H), 1.77 (d, J=6.3, 4H), 1.61 (m, 4H), 1.4–0.8 (overlapping signals, 30H). $^{31}$P NMR (CDCl3): δ−9.8.

Ligand 4

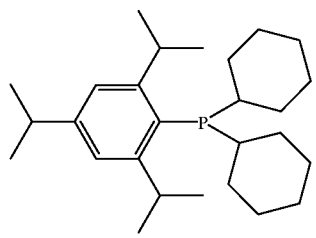

Example 12

This is an example of Pd/ligand 4-catalyzed aryl amination reaction for aryl amine synthesis. A reaction tube containing NaO$^t$Bu (120 mg, 1.25 mmol) was thoroughly evacuated and purged with argon. 5-Chloro-m-xylene (0.14 mL, 1.04 mmol), heptylmethylamine (0.21 mL, 1.25 mmol), a toluene solution of Pd(dba)$_2$ (1.2 mL, 1.0 mg/mL, 2.1 μmol) and a toluene solution of ligand 4 (2.5 mL, 1.0 mg/mL, 6.2 μmol) and toluene (0.3 mL) were added to the reaction tube and the reaction was heated at 105° C. for 21.5 h. The reaction was taken up in ether (100 mL) and washed with H$_2$O (30 mL) and brine (30 mL). The organic phase was dried over MgSO$_4$, filtered and concentrated under vacuum. The crude product was purified by column chromatography on silica gel using hexanes/ethyl acetate as eluant to afford compound 2 (shown below in Table 1) as a yellowish oil (239 mg, 98%) after drying under vacuum. $^1$H NMR (CDCl$_3$): δ6.33 (br, 3H, ArH), 3.25 (t, J=7.6, 2H, —NCH$_2$—), 2.89 (s, 3H, —N—CH$_3$), 2.27 (s, 6H, Ar(CH$_3$)$_2$), 1.54 (br, 2H, —NCH$_2$CH$_2$—), 1.30 (br, 8H, —(CH$_2$)$_4$CH$_3$), 0.89 (br t, J=6.6, 3 H, —CH$_3$).

Example 13

This is an example of Pd/ligand 4-catalyzed aryl amination reaction for aryl amine synthesis. The compound 3 (shown below in Table 1) was obtained as a yellowish oil (188 mg, 95%) from the reaction of 5-chloro-m-xylene (0.14 mL, 1.04 mmol), morphorline (0.11 mL, 1.26 mmol), NaO$^t$Bu (120 mg, 1.25 mmol), Pd(dba)$_2$ (1.2 mg, 2.1 μmol) and ligand 4 (2.5 mg, 6.2 μmol) in toluene at 105° C. for 6 h. $^1$H NMR (CDCl$_3$): δ6.60 (s, 3H, ArH), 3.88 (t, J=4.8, 4H, —O—(CH$_2$)$_2$—), 3.17 (t, J=4.8, 4H, —O —(CH$_2$)$_2$—), 2.34 (s, 6H, CH$_3$'s).

Example 14

This is an example of Pd/ligand 4-catalyzed aryl amination reaction for aryl amine synthesis. The compound 4 (shown below in Table 1) was obtained as a yellowish oil (239 mg, 79%) from the reaction of 4-chlorobenzophenone (217 mg, 1.0 mmol), N-benzylmethylamine (0.15 mL, 1.16 mmol), NaO$^t$Bu (115 mg, 1.20 mmol), Pd(dba)$_2$ (0.56 mg, 1.0 μmol) and ligand 4 (1.2 mg, 3.0 μmol) in toluene at 105° C. for 26 h. $^1$H NMR (CDCl$_3$): δ7.83 (d, J=9.0, 2H, ArH), 7.75 (d, J=6.8, 2H, ArH), 7.58 –7.22 (m, 8H, ArH), 6.77 (d, J=8.9, 2H, ArH), 4.69 (s, 2H, —N—CH$_2$Ph), 3.19 (s, 3H, —NCH$_3$).

Example 15

This is an example of Pd/ligand 4-catalyzed aryl amination reaction for aryl amine synthesis. The compound 5 (shown below in Table 1) was obtained as a yellowish oil (234 mg, 97%) from the reaction of 2-chloroanisole (0.13 mL, 1.02 mmol), octylamine (0.20 mL, 1.21 mmol), NaO$^t$Bu (118 mg, 1.23 mmol), Pd(dba)$_2$ (6 mg, 10 μmol) and ligand 4 (13 mg, 32 μmol) in toluene at 105° C. for 5 h. $^1$H NMR (CDCl$_3$): δ6.92 (t, J=7.6, 1H, ArH), 6.81 (d, J=7.6, 1H, ArH), 6.71 (d, J=7.6, 1H, ArH), 6.67 (t, J=7.6, 1H, ArH), 4.22 (br, 1H,—NH), 3.86 (s, 3H, —OCH$_3$), 3.16 (t, J=7.2, 2H, —NCH$_2$—), 1.69 (pentet, 2H, —NCH$_2$CH$_2$CH$_2$—), 1.35 (br, 10H, —CH$_2$—'s), 0.95 (br, 3H, CH$_3$).

Example 16

This is an example of Pd/ligand 4-catalyzed Suzuki reaction for biaryl synthesis. A solid mixture of Na$_2$CO$_3$ (369 mg, 3.5 mmol), 2-chlorobenzonitrile (239 mg, 1.7 mmol), and p-tolueneboronic acid (355 mg, 2.6 mmol), Pd(dba)$_2$ (1 mg, 1.7 μmol), and ligand 4 (7 mg, 17 μmol) was evacuated thoroughly and purged with argon. Toluene (3 mL) and deoxygenated H$_2$O (1 mL) were added and the reaction mixture was heated at 95° C. After 3 h, GC-MS analysis showed a conversion of >99% based on the disappearance of 2-chlorobenzonitrile and a selectivity of >99% for the desired product 2-cyano-4'-methylbiphenyl (compound 6, Table 1) over 4,4'-dimethylbiphenyl.

Example 17

This is an example of Pd/ligand 4-catalyzed Suzuki reaction for biaryl synthesis. A solid mixture of Na$_2$CO$_3$ (369 mg, 3.5 mmol), 2-chlorobenzonitrile (239 mg, 1.7 mmol), and p-tolueneboronic acid (355 mg, 2.6 mmol) and ligand 4 (4 mg, 10 μmol) was degassed thoroughly and purged with argon. A toluene solution of Pd(dba)$_2$ (0.5 mL, 1 mg Pd(dba)$_2$/mL, 0.9 μmol), toluene (3 mL) and deoxygenated H$_2$O (1 mL) were added and the reaction mixture was heated at 95° C. After 3 h, GC-MS analysis showed a conversion of >99% based on the disappearance of 2-chlorobenzonitrile and a selectivity of >99% for the desired product 2-cyano-4'-methylbiphenyl (compound 6, Table 1) over 4,4'-dimethylbiphenyl.

Example 18

This is an example of Pd/ligand 4-catalyzed Suzuki reaction for biaryl synthesis. A solid mixture of Na$_2$CO$_3$ (369 mg, 3.5 mmol), 2-chlorobenzonitrile (239 mg, 1.7 mmol), and p-tolueneboronic acid (355 mg, 2.6 mmol) and ligand 4 (3 mg, 7 μmol) was evacuated thoroughly and purged with argon. A toluene solution of Pd(dba)$_2$ (0.2 mL, 1 mg Pd(dba)$_2$/mL, 0.3 μmol), toluene (3 mL) and deoxygenated H$_2$O (1 mL) were added and the reaction mixture was heated at 95° C. After 3 h, GC-MS analysis showed a conversion of >99% based on the disappearance of 2-chlorobenzonitrile and a selectivity of >99% for the desired product 2-cyano-4'-methylbiphenyl (compound 6, Table 1) over 4,4'-dimethylbiphenyl. The reaction was taken up in diethyl ether (100 mL) and washed with water (30 ml) and brine (30 ml). The organic phase was dried over MgSO$_4$ and concentrated under vacuum. The crude residue was column chromatographed on silica gel using hexane:EtOAc (4:1) as eluent to afford 323 mg (96% yield) of 2-cyano-4'-methylbiphenyl (6) as an off-white solid.

Example 19

This is an example of Pd/ligand 4-catalyzed Suzuki reaction for biaryl synthesis. A solid mixture of K$_3$PO$_4$ (425 mg, 2.0 mmol) and p-tolueneboronic acid (204 mg, 1.5 mmol) was thoroughly evacuated and purged with argon. A toluene solution of Pd(dba)$_2$/ligand 4 (1 mg Pd(dba)$_2$/mL, 1.7 μmol, Pd/ligand mole ratio=1:3,), 2'-chloroacetonphenone (0.13 mL, 1.0 mmol) and toluene (3.0 mL) were added. The reaction mixture was heated at 100° C. After 1 h, GC-MS analysis showed a conversion of >99% based on the disappearance of 2'-chloroacetonphenone and a selectivity of >99% for the desired product 2-acetyl-4'-methyl-biphenyl (compound 7, Table 1) over 4,4'-dimethylbiphenyl.

Example 20

This is an example of Pd/ligand 4-catalyzed Suzuki reaction for biaryl synthesis. A solid mixture of CsF (450 mg, 3.0 mmol) and p-tolueneboronic acid (204 mg, 1.5 mmol) was thoroughly evacuated and purged with argon. A toluene solution of Pd(dba)$_2$/ligand 1 (1 mL, 1 mg Pd(dba)$_2$/mL, 1.7 μmol, Pd/ligand mole ratio=1:3), 2'-chloroacetophenone (0.13 mL, 1.0 mmol) and toluene (3.0 mL) were added. The reaction mixture was heated at 100° C. After 1 h, GC-MS analysis showed a conversion of >99% based on the disappearance of 2'-chloroacetonphenone and a selectivity of >99% for the desired product 2-acetyl-4'-methyl-biphenyl (compound 7, Table 1) over 4,4'-dimethylbiphenyl.

TABLE 1

Pd/Ligand 4-Catalyzed Aryl Amination and Suzuki Reactions

TABLE 1-continued

Pd/Ligand 4-Catalyzed Aryl Amination and Suzuki Reactions

| Starting Materials | Product |
|---|---|
| 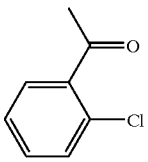 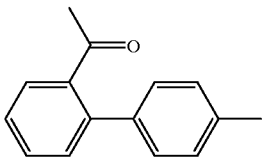 | 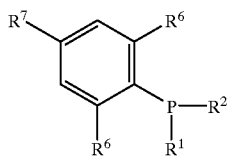 |

7

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A transition metal catalyzed process comprising providing reactants and reacting said reactants in the presence of
   (1) a ligand characterized by the general formula

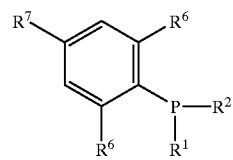

wherein each $R^1$ and $R^2$ is independently selected from the group consisting of alkyl, substituted alkyl, cycloalkyl and substituted cycloalkyl;
   each of $R^6$ is independently selected from the group consisting of alkyl, substituted alkyl, cycloalkyl, substituted cycloalkyl, heteroalkyl, substituted heteroalkyl, heterocycloalkyl, substituted heterocycloalkyl, heteroaryl, substituted heteroaryl, silyl, amino, nitro, ester, acid, alkoxy, aryloxy, hydroxy, transition metals, COOH, $SO_3G$ (wherein G is selected from the group consisting of Na, K and H) and combinations thereof;
   $R^7$ is selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, silyl, amino, nitro, ester, acid, alkoxy, aryloxy, hydroxy, transition metals, COOH, $SO_3G$ (wherein G is selected from the group consisting of Na, K and H) and combinations thereof; and
   (2) a metal precursor compound characterized by the general formula $M(L)_n$, where M is a transition metal selected from the group consisting of Pd, Ni, Fe, Co, Ru, Ir, Rh and Pt; L is independently each occurrence, a ligand; and n is 0, 1, 2, 3, 4, and 5.

2. The process of claim 1, wherein each $R^1$ and $R^2$ is cyclohexyl or substituted cyclohexyl.

3. The process of claim 1, wherein each $R^6$ is independently selected from the group alkyl, substituted alkyl, cycloalkyl and substituted cycloalkyl.

4. The process of claim 1, wherein each $R^6$ is isopropyl.

5. A process for preparing polycyclic aromatic compounds by cross-coupling of a first aromatic compound with a second aromatic compounds in the presence of a base, a solvent, a metal precursor and a ligand that is characterized by the general formula:

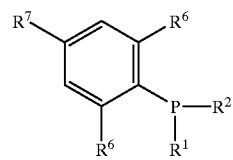

wherein each $R^1$ and $R^2$ is independently selected from the group consisting of alkyl, substituted alkyl, cycloalkyl and substituted cycloalkyl;
   each $R^6$ is independently selected from the group consisting of alkyl, substituted alkyl, cycloalkyl, substituted cycloalkyl, heteroalkyl, substituted heteroalkyl, heterocycloalkyl, substituted heterocycloalkyl, heteroaryl, substituted heteroaryl, silyl, amino, nitro, ester, acid, alkoxy, aryloxy, hydroxy, transition metals, COOH, $SO_3G$ (wherein G is selected from the group consisting of Na, K and H) and combinations thereof;
   $R^7$ is selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, silyl, amino, nitro, ester, acid, alkoxy, aryloxy, hydroxy, transition metals, COOH, $SO_3G$ (wherein G is selected from the group consisting of Na, K and H) and combinations thereof.

6. The process of claim 5, wherein each $R^1$ and $R^2$ is cyclohexyl.

7. The process of claim 5, wherein said base is selected from the group consisting of alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides, alkali metal and alkaline earth metal phosphates, alkali metal and alkaline earth fluorides, ammonium fluorides and primary, secondary and tertiary amines.

8. The process of claim 5, wherein said solvent is selected from the group consisting of ethers, hydrocarbons, alcohols, ketones, amides, nitrites, water and mixtures thereof.

9. The process of claim 5, wherein said first aromatic compound is a compound that is characterized by either of the general formulas

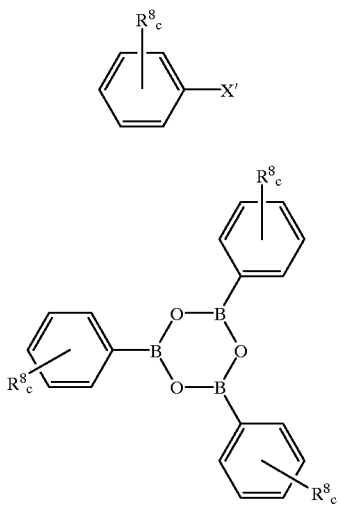

IV

V where $R^8$ is selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; c is 0, 1, 2, 3, 4 or 5 and optionally two or more $R^8$ groups are joined together in a ring structure; X' is selected from the group consisting of $BR^{10}_2$, $B(OR^{10})_2$, $MgQ^1$, $ZnQ^1$, $CuQ^1$, $SiR^{10}_3 SnR^{10}_3$ or Li, wherein each $R^{10}$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; and $Q^1$ is selected from the group consisting of Cl, Br, I or F.

10. The process of claim 5, wherein said second aromatic compound is selected from the group consisting of compounds that are characterized by the general formula:

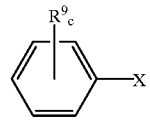

where X is Br, Cl, F, I, tosylates, triflates, or $N_2+$ and $R^9$ is selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; and c is 0, 1, 2, 3, 4 or 5; and optionally two or more $R^9$ groups are joined together in a ring structure.

11. The process of claim 5, wherein the aromatic boronic compound is p-tolueneboronic acid and the aromatic halogen compound is o-chlorobenzonitrile.

12. A compound having the general formula:

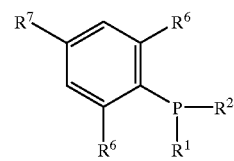

wherein each $R^1$ and $R^2$ is independently selected from the group consisting of alkyl, substituted alkyl, cycloalkyl and substituted cycloalkyl;

each $R^6$ is independently selected from the group consisting of alkyl, substituted alkyl, cycloalkyl, substituted cycloalkyl, heteroalkyl, substituted heteroalkyl, heterocycloalkyl, substituted heterocycloalkyl, heteroaryl, substituted heteroaryl, silyl, amino, nitro, ester, acid, alkoxy, aryloxy, hydroxy, transition metals, COOH, $SO_3G$ (wherein G is selected from the group consisting of Na, K and H) and combinations thereof;

$R^7$ is selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, silyl, amino, nitro, ester, acid, alkoxy, aryloxy, hydroxy, transition metals, COOH, $SO_3G$ (wherein G is selected from the group consisting of Na, K and H) and combinations thereof.

13. The compound of claim 12, wherein each $R^1$ and $R^2$ is cyclohexyl.

14. The compound of claim 12, wherein each $R^6$ is isopropyl.

15. The compound of claim 14, wherein $R^7$ is either isopropyl or hydrogen.

16. A transition metal catalyzed reaction comprising contacting a reactant with the reaction product of a metal precursor and the compound in claim 12.

17. The reaction of claim 16, wherein the reaction forms a C—H, C—C, C—N, C—O, C—S, C—P, C—B or a C—Si bond.

18. The reaction of claim 16, wherein the reaction is an aryl amination reaction.

* * * * *

UNITED STATES PATENT AND TRADEMARK OFFICE
CERTIFICATE OF CORRECTION

PATENT NO. : 6,268,513 B1
DATED : July 31, 2001
INVENTOR(S) : Guram et al.

It is certified that error appears in the above-identified patent and that said Letters Patent is hereby corrected as shown below:

<u>Column 22,</u>
Line 67, the work "nitrites," should be replaced with -- nitriles, --

Signed and Sealed this

Twenty-seventh Day of August, 2002

Attest:

Attesting Officer

JAMES E. ROGAN
*Director of the United States Patent and Trademark Office*